United States Patent [19]
Adolph

[11] 4,048,219
[45] Sept. 13, 1977

[54] ACETALS DERIVED FROM NEGATIVELY SUBSTITUTED ALDEHYDES AND POLYNITRO- OR HALONITROETHANOLS

[75] Inventor: Horst G. Adolph, Beltsville, Md.

[73] Assignee: The United States of America as represented by the Secretary of the Navy, Washington, D.C.

[21] Appl. No.: 640,091

[22] Filed: Dec. 12, 1975

Related U.S. Application Data

[62] Division of Ser. No. 461,554, April 17, 1974, abandoned.

[51] Int. Cl.$^2$ ............................................... C07C 69/66
[52] U.S. Cl. ................................. 560/156; 260/615 A
[58] Field of Search .................................... 260/484 R

[56]   References Cited
U.S. PATENT DOCUMENTS 3,387,044   6/1968   Grakauskas ..................... 260/484 R Primary Examiner—Paul J. Killos
Attorney, Agent, or Firm—R. S. Sciascia; A. L. Branning; R. D. Johnson

[57]   ABSTRACT

Acetals of the formulas $CHCl_2CH(OR)_2$, $CCl_3CH(OR)_2$, $CHF_2CH(OR)_2$, $CF_3CH(OR)_2$, $RO_2CCH(OR)_2$, and $(RO)_2HCCH(OR)_2$ wherein R can be $-CH_2CYZ(NO_2)$, $-CH_2CH_2CYZ(NO_2)$, $-CH_2C(NO_2)_2CH_3$, $-CH_2C(NO_2)_2CYZ(NO_2)$, $-CH_2C(NO_2)_2CH_2CYZ(NO_2)$ or $-CH_2C(NO_2)_2C(NO_2)_2CYZ(NO_2)$ wherein Y and Z vary independently and can be Cl, F or $NO_2$. These acetals are produced by contacting a negatively substituted aldehyde such as $CHCl_2CHO$, $CCl_3CHO$, $CHF_2CHO$, $CF_3CHO$, $HO_2CCHO$, or OHCCHO with a negatively substitute alcohol of the formula ROH wherein R is as defined above. Either $FSO_3H$, $ClSO_3H$, or $CHF_2SO_3H$, or $CF_3SO_3H$ is used to catalyze the condensation. The acetals of this invention are useful as explosives.

3 Claims, No Drawings

ACETALS DERIVED FROM NEGATIVELY SUBSTITUTED ALDEHYDES AND POLYNITRO- OR HALONITROETHANOLS

This is a division of application Ser. No. 461,554 filed Apr. 17, 1974, now abandoned.

BACKGROUND OF THE INVENTION

This invention relates generally to acetals and more particularly to acetals containing nitro groups.

Formals and acetals of polynitro- and halonitroethanols (e.g., 2,2,2-trinitroethanol, 2,2,2-fluorodinitroethanol, 2,2-dinitropropanol, 2,2,2-difluoronitroethanol) are of considerable interest as explosive and propellant ingredients. For example, acetals and formals of 2,2-dinitropropanol and 2,2,2-fluorodinitroethanol have been used extensively as energetic plasticizers in various composite propellants and explosives. Special synthesis methods had to be discovered for the preparation of these materials since the extremely low reactivity of the parent alcohols rendered useless the conventional methods for acetal and formal preparation. Thus, U.S. Pat. No. 3,526,667 describes a method for the preparation of formals of nitroalcohols consisting of the condensation with formaldehyde in concentrated sulfuric acid as reaction medium. A method for the preparation of fluorodinitroalkyl acetals, U.S. Pat. No. 3,629,338, uses $BF_3$ and similar acidic catalysts to effect condensation of acetaldehyde with fluorodinitroalkanols.

However, efforts to employ these methods to prepare acetals and formals derived from aldehydes other than formaldehyde and acetaldehyde have been largely unsuccessful. Especially aldehydes with negative (i.e., electron-withdrawing) substituents were found to be unreactive under the conditions used by these methods. For example, concentrated sulfuric acid fails to catalyze acetal formation between $CCl_3CHO$, $CF_3CHO$, and $HOOCCHO$ aldehydes and $(NO_2)_2FCCH_2OH$.

SUMMARY OF THE INVENTION

Accordingly, one objective of this invention is to provide novel acetals having high explosive energy content.

Another object of this invention is to provide novel explosive acetals which are thermally stable.

A further object of this invention is to provide novel acetals which are derived from negatively substituted aldehydes and polynitro or halonitro alcohols.

A still further object of this invention is to provide a process for reacting polynitro and halonitro alcohols with negatively substituted aldehydes to form high energy acetals.

These and other objects of this invention are accomplished by providing compounds of the formula $CHCl_2CH(OR)_2$, $CCl_3CH(OR)_2$, $CHF_2CH(OR)_2$, $CF_3CH(OR)_2$, $RO_2CCH(OR)_2$, and $(RO)_2CHCH(OR)_2$ wherein R is selected from the group consisting of $-CH_2CYZ(NO_2)$, $-CH_2CH_2CYZ(NO_2)$, $-CH_2C(NO_2)_2CH_3$, $-CH_2C(NO_2)_2CYZ(NO_2)$, $-CH_2C(NO_2)_2CH_2CYZ(NO_2)$, and $-CH_2C(NO_2)_2C(NO_2)_2CYZ(NO_2)$, wherein Y and Z vary independently and are selected from the group consisting of Cl, F, and $NO_2$. These acetals are prepared by using sulfonic acids selected from the group consisting of $CHF_2SO_3H$, $CF_3SO_3H$, $FSO_3H$, and $ClSO_3H$ to catalyze condensation reactions between polynitro or halonitro alcohols and negatively substituted aldehydes.

DETAILED DESCRIPTION OF THE PREFERRED EMBODIMENT

The synthesis of compounds of this invention can be shown by the following general reactions:

(I) $CHCl_2CHO + 2ROH \rightarrow CHCl_2CH(OR)_2 + H_2O$
(II) $CCl_3CHO + 2ROH \rightarrow CCl_3CH(OR)_2 + H_2O$
(III) $CHF_2CHO + 2ROH \rightarrow CHF_2CH(OR)_2 + H_2O$
(IV) $CF_3CHO + 2ROH \rightarrow CF_3CH(OR)_2 + H_2O$
(V) $HO_2CCHO + 3ROH \rightarrow RO_2CCH(OR)_2 + 2H_2O$
(VI) $OHCCHO + 4ROH \rightarrow (RO)_2CHCH(OR)_2 + 2H_2O$ wherein R is selected from the group consisting of $-CH_2CYZ(NO_2)$, $-CH_2CH_2CYZ(NO_2)$, $-CH_2C(NO_2)_2CH_3$, $-CH_2C(NO_2)_2CYZ(NO_2)$, $-CH_2C(NO_2)_2CH_2CYZ(NO_2)$, and $-CH_2C(NO_2)_2C(NO_2)_2CYZ(NO_2)$, wherein Y and Z vary independently and are selected from the group consisting of Cl, F, and $NO_2$.

Equations (I), (II), (III), and (IV) show the general reaction of halo substituted acetaldehydes with polynitro and halonitro alcohols to form acetals. Two molecules of alcohol of the formula ROH react with one molecule of aldehyde selected from the group consisting of $CHCl_2CHO$, $CCl_3CHO$, $CHF_2CHO$, and $CF_3CHO$ to form an acetal selected from the group consisting of $CHCl_2CH(OR)_2$, $CCl_3CH(OR)_2$, $CHF_2CH(OR)_2$, and $CF_3CH(OR)_2$ respectively wherein R is as defined above. Preferred are acetals selected from the group consisting of $CHCl_2CH[OCH_2C(NO_2)_2CH_3]_2$, $CCl_3CH[OCH_2C(NO_2)_2CH_3]_2$, $CHF_2CH[OCH_2C(NO_2)_2CH_3]_2$, $CF_3CH[OCH_2C(NO_2)_2CH_3]_2$, $CHCl_2CH[OCH_2CYZ(NO_2)]_2$, $CCl_3CH[OCH_2CYZ(NO_2)]_2$, $CHF_2CH[OCH_2CYZ(NO_2)]_2$, and $CF_3CH[OCH_2CYZ(NO_2)]_2$, wherein Y and Z vary independently and are selected from the group consisting of Cl, F, and $NO_2$. More preferred are compounds selected from the group consisting of $CCl_3CH[OCH_2C(NO_2)_3]_2$, $CF_3CH[OCH_2C(NO_2)_3]_2$, $CCl_3CH[OCH_2CF(NO_2)_2]_2$, and $CF_3CH[OCH_2CF(NO_2)_2]_2$, with $CCl_3CH[OCH_2CF(NO_2)_2]_2$, and $CF_3CH[OCH_2CF(NO_2)_2]_2$ being the most preferred.

Equation (V) shows the reaction of one molecule of glyoxylic acid $HO_2CCHO$, with 3 molecules of polynitro and halonitro alcohols to form a compound containing both an acetal and an ester group, $RO_2CCH(OR)_2$, wherein R is selected from the group consisting of $-CH_2CYZ(NO_2)$, $-CH_2CH_2CYZ(NO_2)$, $-CH_2C(NO_2)_2CH_3$, $-CH_2C(NO_2)_2CYZ(NO_2)$, $-CH_2C(NO_2)_2CH_2CYZ(NO_2)$, and $-CH_2C(NO_2)_2C(NO_2)_2CYZ(NO_2)$, wherein Y and Z vary independently and are selected from the group consisting of Cl, F, and $NO_2$. Preferred are compounds selected from the group consisting of $CH_3C(NO_2)_2CH_2O_2CCH[OCH_2C(NO_2)_2CH_3]_2$, $(NO_2)_3CCH_2O_2CCH[OCH_2C(NO_2)_3]_2$, $(NO_2)_2FCCH_2O_2CCH[OCH_2CF(NO_2)_2]_2$, and $(NO_2)_2F_2CCH_2O_2CCH[OCH_2CF(NO_2)_2]_2$, with $(NO_2)_2FCCH_2O_2CCH[OCH_2CF(NO_2)_2]_2$ being the most preferred.

Finally equation (VI) shows the reaction of one molecule of glyoxal, $OHCCHO$, with 4 molecules of polynitro or halonitro alcohol to form a diacetal of the formula $(RO)_2CHCH(OR)_2$, wherein R is selected from the group consisting $-CH_2CYZ(NO_2)$, $-CH_2CH_2CYZ(NO_2)$, $-CH_2C(NO_2)_2CH_3$, $-CH_2C(NO_2)_2CYZ(NO_2)$, $-CH_2C(NO_2)CH_2CYZ(NO_2)$, and $-CH_2C(NO_2)_2C(NO_2)_2CYZ(NO_2)$, wherein Y and Z are selected from the group consisting of Cl, F, and $NO_2$.

Preferred are compounds selected from the group consisting of [CH$_3$C(NO$_2$)$_2$CH$_2$O]$_2$CHCH[OCH$_2$C(NO$_2$)$_2$CH$_3$]$_2$, [(NO$_2$)$_3$CCH$_2$O]$_2$CHCH[OCH$_2$C(NO$_2$)$_3$]$_2$, [(NO$_2$)$_2$FCCH$_2$O]$_2$CHCH[OCH$_2$CF(NO$_2$)$_2$]$_2$, and [(NO$_2$)F$_2$CCH$_2$O]$_2$CHCH[OCH$_2$CF$_2$(NO$_2$)], with [(NO$_2$)$_2$FCCH$_2$O]$_2$CHCH[OCH$_2$CF(NO$_2$)$_2$]$_2$ being the most preferred.

Most critical to the synthesis of the compounds of the present invention is the selection of a catalyst. Prior art catalysts such as boron trifluride or concentrated sulfuric acid fail to promote the condensation reactions of the present invention. However, it has been found that acids such as FSO$_3$H, CHF$_2$SO$_3$H, CF$_3$SO$_3$H, and ClSO$_3$H will catalyze the synthesis reactions of the present invention (i.e., equations (I) through (VI)). FSO$_3$H, CHF$_2$SO$_3$H, and CF$_3$SO$_3$H are the preferred catalysts with CF$_3$SO$_3$H being the most preferred catalyst. Other acids of comparable strength may be used. For example, a perfluoroalkylsulfonic acid having from 2 to 5 carbon atoms may be used in place of trifluoromethanesulfonic acid as the catalyst.

The reactions should be conducted in a solvent which is inert to the reactants, products, and catalyst. Methylene chloride, chloroform, carbon tetrachloride, ethylene chloride and similar solvents are suitable.

The present reactions may be run at from 0° to 45° C with 15° to 35° being preferred.

It will be apparent that the method of synthesis of the present invention may be applied to produce cyclic acetals and polymeric acetals by using the appropriate polynitro halonitro polyols.

To more clearly illustrate this invention, the following examples are presented. It should be understood, however, that these examples are presented merely as a means of illustration and are not intended to limit the scope of the invention in any way.

EXAMPLE I

Bis(2,2,2-fluorodinitroethyl)trichloroacetal 10 ml. of anhydrous trifluoromethanesulfonic acid was added dropwise to an ice cooled mixture of 5.6g CCl$_3$CHO and 6.2g 2,2,2-fluorodinitroethanol, CF(NO$_2$)$_2$CH$_2$OH. The initially homogeneous mixture soom became turbid. The mixture was then stirred for 24 hours at ambient temperature. Next, the mixture was poured over crushed ice and the crude product was extracted into methylene chloride. Removal of low-boilers in vacuo left 9g of the crude product containing several minor (total less than 5%) impurities. A pure sample was obtained by running a methylene chloride solution of the crude product through a column of Silica (G. F. Smith, Columbus, Ohio), the impurities being eluted long before the main product, which was obtained as a colorless oil.

Analysis Calculated for C$_6$H$_5$F$_2$Cl$_3$N$_4$O$_{10}$: C, 16.47; H, 1.15; Cl, 24.31; F, 8.69; N, 12.81; m.w. 437.48. Found C, 16.3; H, 1.3; Cl, 24.4; F, 8.8; N, 12.5; m.w. (McCN), 438.

NMR (CDCl$_3$). δ 4.94 d (J$_{HF}$18 cps); δ 5.08 s; area ratio 4:1

EXAMPLE II

Bis(2,2,2-fluorodinitroethyl)trifluoroacetal

A solution of 5.75g of fluoral hydrate, CF$_3$CH(OH)$_2$, and 16.25g of 2,2,2-fluorodinitroethanol, CF(NO$_2$)$_2$CH$_2$OH, in 50 ml of trifluoro methanesulfonic acid was stirred at ambient temperature for 24 hours, then warmed to 40° and stirred an additional 65 hours. The reaction mixture was poured over crushed ice, the product extracted with methylene chloride, and the extracts were washed with 0.1N NaOH solution until the aqueous phase remained colorless. Removing the solvent left 12g of a light brown oil whose main component was Bis(2,2,2-fluorodinitroethyl)trifluoroacetal.

A pure sample of the acetal was obtained by repeated chromatography on Silica (G. F. Smith, Columbus, Ohio) with methylene chloride/hexane (1.5:3.5 to 1.75:3.25) as eluant; progress of the purification was followed by gas chromatographic analysis. The solvents were removed by maintaining the solution at 0.5 mm/40° C for several hours. The purified Bio(2,2,2-fluorodinitroethyl)trifluoroacetal was a light amber oil, M.P. −1° to 0° C.

Analysis Calculated for C$_6$H$_5$F$_5$N$_4$O$_{10}$; C, 18.57; H, 1.30; F, 24.48; N, 14.44; m.w., 388.13, Found: C, 19.0, H, 1.2; F, 25.2; N, 14.7; m.w. (MeCN), 388.

NMR (CDCl$_3$): δ 4.83 d (J$_{HF}$15 cps); δ 5.08 q (J$_{HF}$4 cps); areas ca. 4:1.

EXAMPLE III 2,2,2-Fluorodinitroethyl bis(2,2,2-fluorodinitroethoxy)acetate

A mixture of 4.65g of 2,2,2-fluorodinitroethanol, 0.75g of anhydrous glyoxylic acid, HOOCCHO, and 5 ml of trifluoromethanesulfonic acid was stirred at ambient temperature of 24 hours. After pouring over crushed ice, the product was extracted into methylene chloride, the extracts were dried and the solvent removed to give 5.1g of 2,2,2-fluorodinitroethyl bis(2,2,2-fluorodinitroethoxy)acetate, a colorless oil. Filtration in methylene chloride solution through a column of Silica (G. F. Smith, Columbus, Ohio) removed 2,2,2-fluorodinitroethanol and other minor impurities, yielding a product of analytic purity M.P. 34.5°–35.5° C.

Analysis: Calculated for C$_8$H$_7$F$_3$N$_6$O$_{16}$: C, 19.21; H, 1.41; F, 11.40; m.w., 500.18. Found: C, 19.2; H, 1.4; F, 11.0; m.w. (MeCN), 493.

NMR (CDCl$_3$): two overlapping AB quartets centered near δ 4.75 and δ 4.92 (acetal CH$_2$ protons); δ 5.29 d (J$_{HF}$16 cps; ester CH$_2$ protons) δ 5.30 s.

EXAMPLE IV 2,2,2-Trinitroethyl bis(2,2,2-trinitroethoxy)acetate

Trifluoromethanesulfonic acid, 7.5 ml, was added with cooling to a mixture of 5.43g trinitroethanol and 0.75g glyoxylic acid. After stirring for 24 hours at ambient temperature, the mixture was poured over crushed ice, the precipitate filtered off and washed with water. Obtained was 4.6g (79%) crude product; mp after recrystallization from ethylene chloride/carbon tetrachloride 100°–101.5° C.

Analysis: Calculated for C$_8$H$_7$N$_9$O$_{22}$: C, 16.53; H, 1.21; N, 21.69; m. w. 581.20. Found C, 16.6; H, 1.2; N, 21.3; m. w. (MeCN), 542.

NMR (CDCl$_3$): δ 5.07, 5.10 two overlapping singlets (acetal CH$_2$ protons); δ 5.51 s (ester CH$_2$); δ 5.53 s (CH); area ratio of signals near 5.1 to signals near 5.5 ca. 4:3.

EXAMPLE V 2,2,2-Difluoronitroethyl bis(2,2,2-difluoronitroethoxy)acetate

Trifluoromethanesulfonic acid, 10 ml, was added with ice-cooling and vigorous stirring to a mixture of 7.7g 2,2,2-difluoronitroethanol and 1.5g glyoxylic acid. Next, the mixture was stirred for 24 hours at ambient temperature. The mixture was then poured over crushed ice and the product extracted into methylene chloride. The extracts were washed with water, dried over magnesium sulfate and freed from solvent in vacuo to give 8.5g crude dialkoxy ester. The product was purified by filtration, in methylene chloride-hexane solution, through a column of Silica to give a material of 98+% purity (gas chromotographic analysis); mp −3° to −2° C, d(20° C) 1.63.

EXAMPLE VI

Tetrakis (2,2,2-fluorodinitroethoxy)ethane

To a mixture of 6.2g of 2,2,2-fluorodinitroethanol and 0.58g glyoxal trimer was added with ice-cooling 7.5 ml trifluoromethanesulfonic acid. The mixture was stirred 50 hours at ambient temperature and poured over crushed ice. The precipitate was filtered off and dried to give 3.25g (50.6% yield) of crude product. The product was purified by recrystallization from ethylene chloride/carbon tetrachloride. The solid product had a melting point of 106.5°–107.5° C.

Analysis: Calculated for $C_{10}H_{10}F_4N_8O_{20}$: C, 18.82; H, 1.58; N, 17.56; F, 11.91; m. w. 638.24. Found: C, 19.2; H, 1.6; N, 17.4; F, 11.7; m. w. (MeCN, MEK), 674, 618.

NMR (CDCl$_3$/acetone-d): δ 4.84 ($J_{HF}$16 cps); δ 4.97 s; areas ca 4:1.

EXAMPLE VII

Tetrakis(2,2,2-trinitroethoxy)ethane

A mixture of 1.16g glyoxal trimer, 14.50g 2,2,2-trinitroethanol and 15 ml trifluoromethanesulfonic acid was stirred at ambient temperature for 48 hours, then poured over crushed ice, the solid filtered off and allowed to dry in air to give 6.25g crude product. The main product is separated from an impurity by fractional crystallization from carbon tetrachloride, acetonitrile or ethylene dichloride, where the by-product is considerably less soluble; mp (from ethylene chloride) 167°–168° C (dec.).

Analysis: Calculated for $C_{10}H_{10}N_{12}O_{28}$: C,16,09; H, 1.35; N, 22.52 m. w., 746.26. Found: C, 16.4; H, 1.4; N, 22.2; m. w., (MeCN), 737.

NMR (CD$_3$CN—C$_6$D$_6$): δ 5.05 s; δ 5.12, 5.14 two overlapping singlets; areas ca. 1:4.

What is claimed as new and desired to be secured by Letters Patent of the United States is:

1. A compound which is RO$_2$CCH(OR)$_2$ wherein R is selected from the group consisting of —CH$_2$CYZ(NO$_2$) and —CH$_2$C(NO$_2$)$_2$CH$_3$ wherein Y and Z vary independently and are selected from the group consisting of Cl, F, and NO$_2$.

2. A compound according to claim 1 which is selected from the group consisting of (NO$_2$)$_3$CCH$_2$O$_2$CCH[OCH$_2$C(NO$_2$)$_3$]$_2$ and (NO$_2$)$_2$FCCH$_2$O$_2$CCH[OCH$_2$CF(NO$_2$)$_2$]$_2$.

3. A compound according to claim 2 which is (NO$_2$)$_2$FCCH$_2$O$_2$CCH [OCH$_2$CF(NO$_2$)$_2$]$_2$.

* * * * *